US009521969B2

(12) United States Patent
Hirabara et al.

(10) Patent No.: US 9,521,969 B2
(45) Date of Patent: Dec. 20, 2016

(54) BIOLOGICAL SIGNAL MEASURING SYSTEM AND BIOLOGICAL SIGNAL MEASURING APPARATUS

(71) Applicant: NIHON KOHDEN CORPORATION, Tokyo (JP)

(72) Inventors: Hideaki Hirabara, Tokyo (JP); Naoki Kobayashi, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 199 days.

(21) Appl. No.: 14/161,566

(22) Filed: Jan. 22, 2014

(65) Prior Publication Data

US 2014/0213884 A1 Jul. 31, 2014

(30) Foreign Application Priority Data

Jan. 31, 2013 (JP) .................................. 2013-017233

(51) Int. Cl.
*A61B 5/05* (2006.01)
*A61B 5/1455* (2006.01)
(Continued)

(52) U.S. Cl.
CPC ........... *A61B 5/1455* (2013.01); *A61B 5/0053* (2013.01); *A61B 5/0261* (2013.01); *A61B 5/6826* (2013.01); *A61B 2505/01* (2013.01)

(58) Field of Classification Search
CPC . A61B 5/021; A61B 5/02438; A61B 5/02444; A61B 5/4818; A61B 5/022
See application file for complete search history.

(56) References Cited

U.S. PATENT DOCUMENTS

| 4,832,484 A | 5/1989 | Aoyagi |
| 6,491,647 B1 * | 12/2002 | Bridger ................. A61B 5/021 |
| | | 128/900 |

(Continued)

FOREIGN PATENT DOCUMENTS

| JP | 63-111837 A | 5/1988 |
| JP | 11-089808 A | 4/1999 |

(Continued)

OTHER PUBLICATIONS

The extended European Search Report for the related European Patent Application No. 14152096.5 dated May 23, 2014.
Japanese Office action for 2013-017233 dated Jun. 28, 2016.

*Primary Examiner* — Joel Lamprecht
(74) *Attorney, Agent, or Firm* — Pearne & Gordon LLP (57) ABSTRACT

A biological signal measuring system includes: a light emitter emitting a first light beam and a second light beam; a light receiver outputting first and second signals in accordance with light intensities of the first and second light beams that have been passed through or reflected from a living tissue of a subject; a first calculating section acquiring a light attenuation of the first and second light beams based on the first and second signals; a second calculating section acquiring a blood-derived light attenuation based on the light attenuation of the first and second light beams; a third calculating section identifying a blood fill time for filling the living tissue, based on a temporal change of the blood-derived light attenuation associated with pressurization of the living tissue; and an outputting section outputting the identified blood fill time.

9 Claims, 6 Drawing Sheets

(51) Int. Cl.
*A61B 5/00* (2006.01)
*A61B 5/026* (2006.01)

(56) References Cited

U.S. PATENT DOCUMENTS

| | | | |
|---|---|---|---|
| 8,977,348 B2* | 3/2015 | Su ........................ | A61B 5/7221 600/407 |
| 2004/0092805 A1 | 5/2004 | Yarita | |
| 2004/0249252 A1 | 12/2004 | Fine et al. | |
| 2007/0282182 A1 | 12/2007 | Messerges et al. | |
| 2012/0130211 A1 | 5/2012 | Kobayashi et al. | |
| 2013/0211291 A1* | 8/2013 | Tran .................... | G06F 19/3418 600/595 |

FOREIGN PATENT DOCUMENTS

| | | |
|---|---|---|
| JP | 2004-202218 A | 7/2004 |
| JP | 2009-125402 A | 6/2009 |
| JP | 2012-115640 A | 6/2012 |
| WO | 2011/078882 A1 | 6/2011 |

* cited by examiner

BIOLOGICAL SIGNAL MEASURING SYSTEM AND BIOLOGICAL SIGNAL MEASURING APPARATUS

CROSS-REFERENCE TO RELATED APPLICATION(S)

This application is based upon and claims the benefit of priority from prior Japanese patent application No. 2013-017233, filed on Jan. 31, 2013, the entire contents of which are incorporated herein by reference.

BACKGROUND

The presently disclosed subject matter relates to a biological signal measuring system, and more particularly to a system for, after pressing living tissue, identifying a time period for filling the living tissue with blood (hereinafter, the time period is referred to as the blood fill time), based on a biological signal acquired from a subject that is an example of the living body. The presently disclosed subject matter relates also to a biological signal measuring apparatus which is to be used in the system.

Measurement of the blood fill time is a technique which is used in the field of emergency medicine in order to determine necessity/unnecessity of transfusion or the priority in a scene of triage. Specifically, a medical person pressurizes living tissue of the subject, such as a fingertip, and visually checks a change of the color of the skin after the pressurization is released. If the color returns to the original color within two seconds, it is determined that the subject is in a normal condition. However, the technique where living tissue is pressed by the hand, and a change of the color of the skin is visually checked has low quantitatively. Moreover, an error due to the measuring person easily occurs.

Therefore, a method has been proposed in which a pulse oximeter is used in measurement of the blood fill time (for example, see JP-A-2012-115640). Specifically, a light beam of a wavelength which allows the light beam to be absorbed into blood is incident on living tissue such as a fingertip, and the intensity of the light beam which is transmitted through the living tissue is measured (hereinafter, the intensity is referred to as the transmitted light intensity). When a portion of the living tissue is pressurized, blood is evacuated from the portion, and therefore the transmitted light intensity is increased. When the pressurization is released, the portion is filled with blood, and therefore the transmitted light intensity is decreased. The blood fill time is identified based on the time period which elapses after the release of the pressurization until the transmitted light intensity returns to the original level.

Figure 6A:
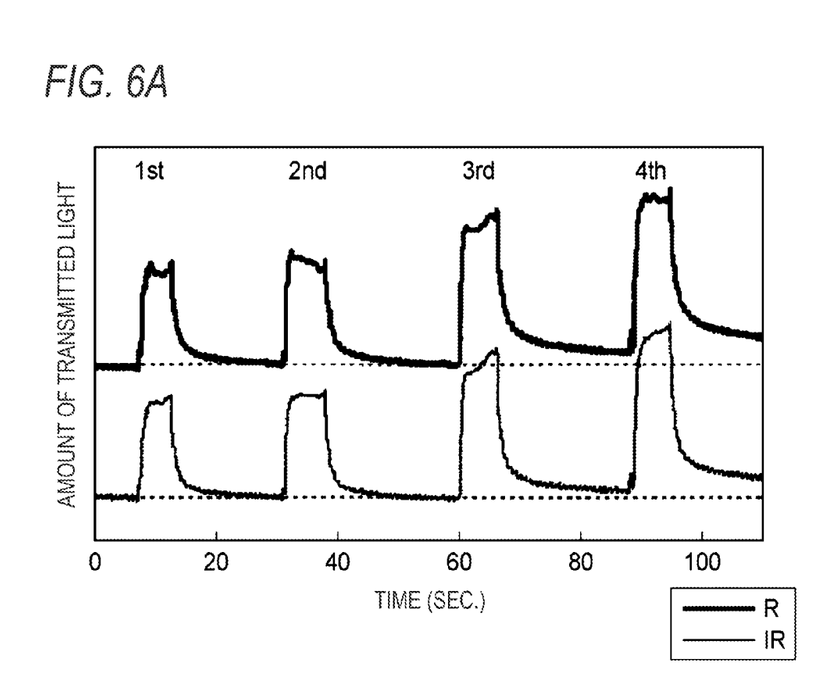
FIGS. 6A and 6B are views illustrating a problem in the case where the blood fill time is identified by a related-art method.
Figure 6B:
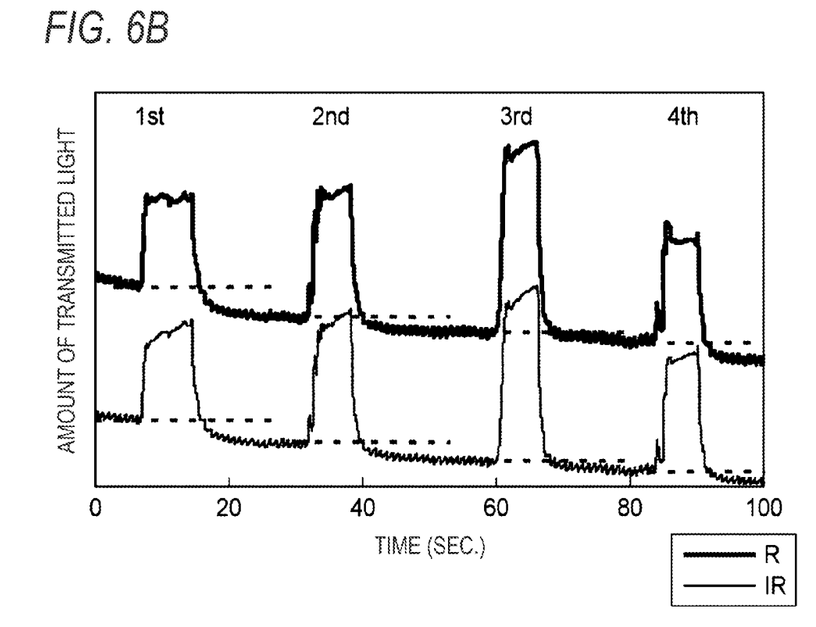

A difference in intensity of pressurization on living tissue may affect results of identifications of the blood fill time. FIGS. 6A and 6B show results of plural identifications of the blood fill time which were performed while changing the pressurization intensity. FIG. 6A shows results in the case where, even where pressurization was released, the transmitted light intensity did not return to the original level. FIG. 6B shows results in the case where, as the measurement was repeated, the reference value of the transmitted light intensity was gradually reduced.

It is supposed that the results shown in FIG. 6A were caused by the phenomenon that deformed tissue is made to hardly return to the original state by strong or repeated pressurization, and the blood portion requires a long time for having the original thickness. It is supposed that the results shown in FIG. 6B were caused by the phenomenon that, conversely, the blood flow is promoted by pressurization, and the thickness of the blood portion is increased. In both the cases, as far as the blood fill time is identified based on the time period which elapses until the transmitted light intensity returns to the state that is attained before pressurization, the results inevitably involve an error. However, pressurization on living tissue is manually performed by a medical person, and therefore it is difficult to always perform pressurization at a constant strength.

SUMMARY

The presently disclosed subject matter may provide a technique in which the blood fill time can be correctly identified by a simple method.

There may be provided a biological signal measuring system comprising: a light emitter which is configured to emit a first light beam having a first wavelength, and a second light beam having a second wavelength; a light receiver which is configured to output first and second signals respectively in accordance with received light intensities of the first and second light beams that have been passed through or reflected from a living tissue of a subject; a first calculating section which is configured to acquire a light attenuation of the first light beam based on the first signal, and a light attenuation of the second light beam based on the second signal; a second calculating section which is configured to acquire a blood-derived light attenuation based on the light attenuation of the first light beam, and the light attenuation of the second light beam; a third calculating section which is configured to identify a blood fill time for filling the living tissue, based on a temporal change of the blood-derived light attenuation associated with pressurization of the living tissue; and an outputting section which is configured to output the identified blood fill time.

The second calculating section may acquire the blood-derived light attenuation based on a difference of the light attenuation of the first light beam and the light attenuation of the second light beam.

The second calculating section may apply a rotation matrix to the light attenuation of the first light beam and the light attenuation of the second light beam, thereby acquiring the blood-derived light attenuation.

The biological signal measuring system may further comprise a fourth calculating section which is configured to acquire a signal in which a component of a frequency that is lower than a predetermined frequency is removed from a signal indicative of the blood-derived light attenuation, and the third calculating section may identify the blood fill time based on a temporal change of the signal which is acquired by the fourth calculating section after the pressurization of the living tissue is released.

The biological signal measuring system may further comprise a fifth calculating section which is configured to acquire a logarithm of a value of the signal acquired by the fourth calculating section, and the third calculating section may identify the blood fill time based on a gradient of a regression line which is obtained from a temporal change of the logarithm after the pressurization of the living tissue is released.

When an amount of the change of the blood-derived light attenuation is larger than a predetermined value, a measurement of the blood fill time by the third calculating section may be automatically started.

The biological signal measuring system may further comprise: a cuff which is adapted to be attached to the subject in a manner that the cuff can pressurize the living tissue; and a cuff pressure controlling section which is configured to control an air pressure inside the cuff.

There may be provided a biological signal measuring apparatus comprising: a signal receiving section which is configured to receive a first signal corresponding to an intensity of a first light beam that has been passed through or reflected from a living tissue of a subject, and that has a first wavelength, and a second signal corresponding to an intensity of a second light beam that has been passed through or reflected from the living tissue, and that has a second wavelength; a first calculating section which is configured to acquire a light attenuation of the first light beam based on the first signal, and a light attenuation of the second light beam based on the second signal; a second calculating section which is configured to acquire a blood-derived light attenuation based on the light attenuation of the first light beam, and the light attenuation of the second light beam; and a third calculating section which is configured to identify a blood fill time for filling the living tissue, based on a temporal change of the blood-derived light attenuation associated with pressurization of the living tissue.

There may be provided a method of controlling a biological signal measuring apparatus comprising a signal receiving section which is configured to receive a first signal corresponding to an intensity of a first light beam that has been passed through or reflected from a living tissue of a subject, and that has a first wavelength, and a second signal corresponding to an intensity of a second light beam that has been passed through or reflected from the living tissue, and that has a second wavelength, the method comprising: acquiring a light attenuation of the first light beam based on the first signal, and a light attenuation of the second light beam based on the second signal; acquiring a blood-derived light attenuation based on the light attenuation of the first light beam, and the light attenuation of the second light beam; identifying a blood fill time for filling the living tissue, based on a temporal change of the blood-derived light attenuation associated with pressurization of the living tissue; and outputting the identified blood fill time.

There may be provided a program causing a computer to execute the method.

There may be provided a non-transitory computer-readable recording medium storing a program causing a computer to execute the method.

DETAILED DESCRIPTION OF EXEMPLARY EMBODIMENTS

An embodiment of the presently disclosed subject matter will be described in detail with reference to the accompanying drawings. In the drawings which will be used in the following description, the scale is adequately changed in order to draw components in a recognizable size.

Figure 1:
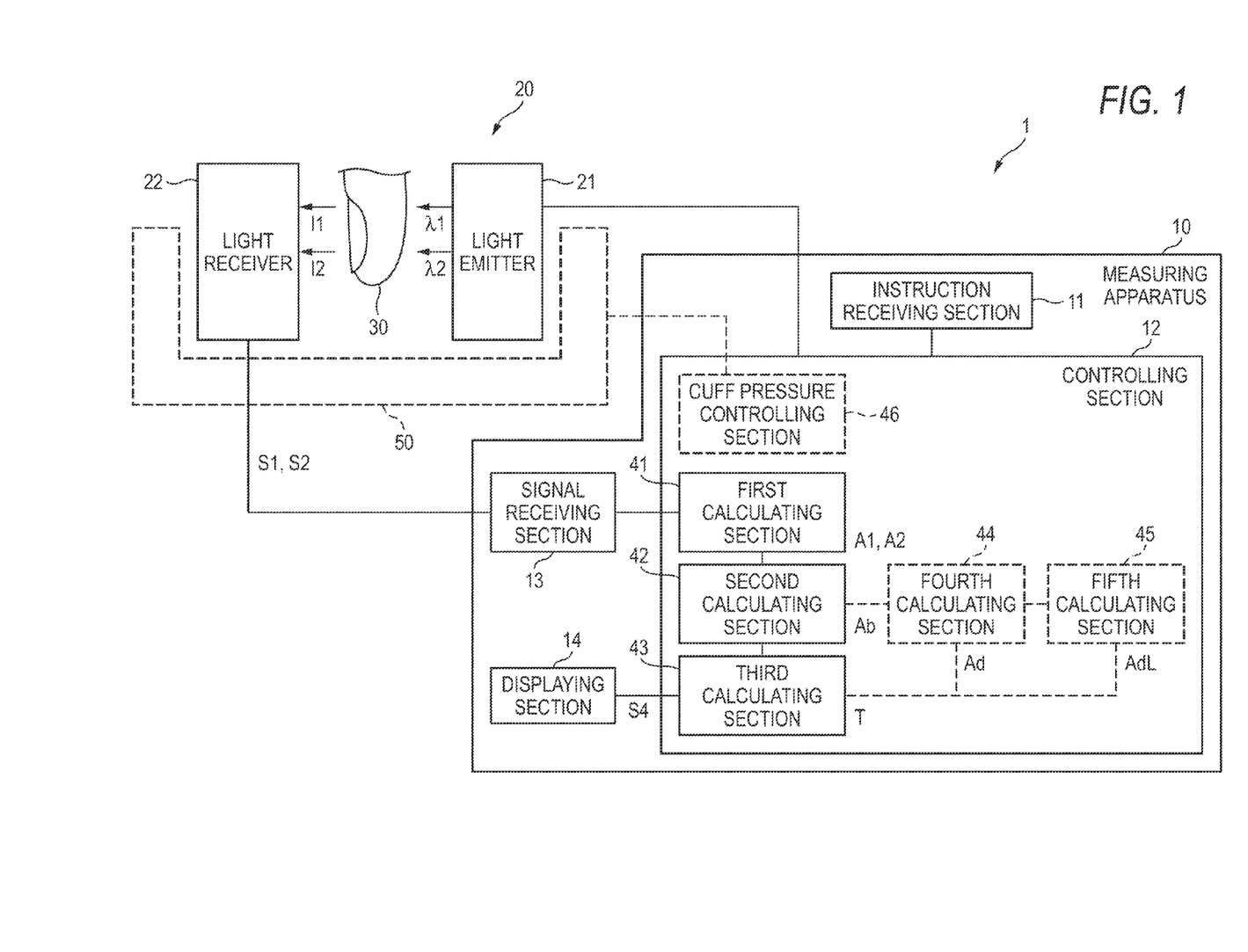
FIG. 1 is a functional block diagram showing the configuration of a biological signal measuring system of an embodiment of the presently disclosed subject matter.

As shown in FIG. 1, a biological signal measuring system 1 of an embodiment of the presently disclosed subject matter includes a measuring apparatus 10 and a probe 20. The measuring apparatus 10 includes an instruction receiving section 11, a controlling section 12, a signal receiving section 13, and a displaying section 14. The probe 20 has a related-art configuration which is to be attached to the finger 30 of the subject, and includes a light emitter 21 and a light receiver 22.

The instruction receiving section 11 is a related-art man-machine interface which is disposed on the outer surface of the measuring apparatus 10, and configured so as to be able to receive instructions which are input by the user in order to cause the measuring apparatus 10 to perform a desired operation.

The controlling section 12 includes: a CPU which performs various calculation processes; a ROM which stores various control programs; a RAM which is used as a working area for storing data and executing the programs; and the like, and performs various controls in the measuring apparatus 10. The controlling section 12 is communicably connected to the instruction receiving section 11. The instruction receiving section 11 supplies a signal corresponding to the received instructions, to the controlling section 12.

The light emitter 21 of the probe 20 is communicably connected to the controlling section 12 of the measuring apparatus 10. The light emitter 21 can emit a first light beam having a first wavelength $\lambda 1$, and a second light beam having a second wavelength $\lambda 2$. In the embodiment, the light emitter 21 includes a light emitting diode which emits a red light beam of 660 nm that is an example of the first wavelength $\lambda 1$, and another light emitting diode which emits an infrared light beam of 940 nm that is an example of the second wavelength $\lambda 2$. In accordance with a control signal supplied from the controlling section 12, each of the light emitting diodes emits the light beam at predetermined timings. The emitted first and second light beams enter the finger 30 which is an example of the living tissue.

The light receiver 22 of the probe 20 is placed at a position where the first and second light beams which have been passed through the finger 30 can be received. The light receiver 22 is configured so as to be able to output a first signal S1 corresponding to the intensity I1 of the received first light beam, and a second signal S2 corresponding to the intensity I2 of the received second light beam. In the embodiment, photodiodes are used as devices having such a configuration. The light receiver 22 is communicably connected to the signal receiving section 13 of the measuring apparatus 10. The signals S1, S2 which are output from the light receiver 22 are supplied to the signal receiving section 13.

The signal receiving section 13 is communicably connected to the controlling section 12. The signal receiving section 13 supplies the received signals S1, S2 to the controlling section 12. The controlling section 12 includes a first calculating section 41, a second calculating section 42, and a third calculating section 43.

The first calculating section 41 is configured so as to acquire the light attenuation A1 of the first light beam based on the first signal S1, and the light attenuation A2 of the second light beam based on the second signal S2. Each of the light attenuations A1, A2 is calculated as a ratio of the amount of light of the first or second signal S1 or S2 received at a certain time (for example, during pressurization of the living tissue) to that at another time (for example, before pressurization of the living tissue), and indicated by either of the following expressions:

$$A1=\log(I1/Io1) \quad (1)$$

$$A2=\log(I2/Io2) \quad (2)$$

where Io1 and Io2 indicate the amounts of received light at the reference time (for example, before pressurization of the living tissue), and I1 and I2 indicate the amounts of received light at the measurement. The suffix "1" indicates the first light beam, and the suffix "2" indicates the second light beam.

The second calculating section 42 is configured so as to acquire the blood-derived light attenuation based on the light attenuations A1, A2 of the first and second light beams acquired by the first calculating section 41. Specifically, the section is configured so as to acquire the blood-derived light attenuation Ab based on the difference of the light attenuation A1 and the light attenuation A2. The principle of the process will be described in detail below.

A change A in light attenuation which is produced when the finger 30 is pressed to change the thickness of the living tissue is caused by a change in thickness of blood and that of thickness of the tissue other than blood (hereinafter, such tissue is referred to as non-blood tissue). This fact indicated by the following expressions:

$$A1=Ab1+At1=E1HbDb+Z1Dt \quad (3)$$

$$A2=Ab2+At2=E2HbDb+Z2Dt \quad (4)$$

where E indicates the absorption coefficient (dl $g^{-1}cm^{-1}$), Hb indicates the hemoglobin concentration (g $dl^{-1}$), Z indicates the light attenuation factor ($cm^{-1}$) of the non-blood tissue, and D indicates the changed thickness ($cm^{-1}$). The suffix "b" indicates blood, the suffix "t" indicates the non-blood tissue, the suffix "1" indicates the first light beam, and the suffix "2" indicates the second light beam.

The wavelength dependency of the non-blood tissue can be neglected. Therefore, it can be deemed that Z1=Z2. When Expression (3) is subtracted from Expression (4), the following is obtained:

$$A2-A1=(E2-E1)HbDb \quad (5).$$

The right side contains only information of blood. When the difference of the light attenuation A1 and the light attenuation A2 is obtained, therefore, it is possible to acquire the blood-derived light attenuation Ab.

Figure 2:
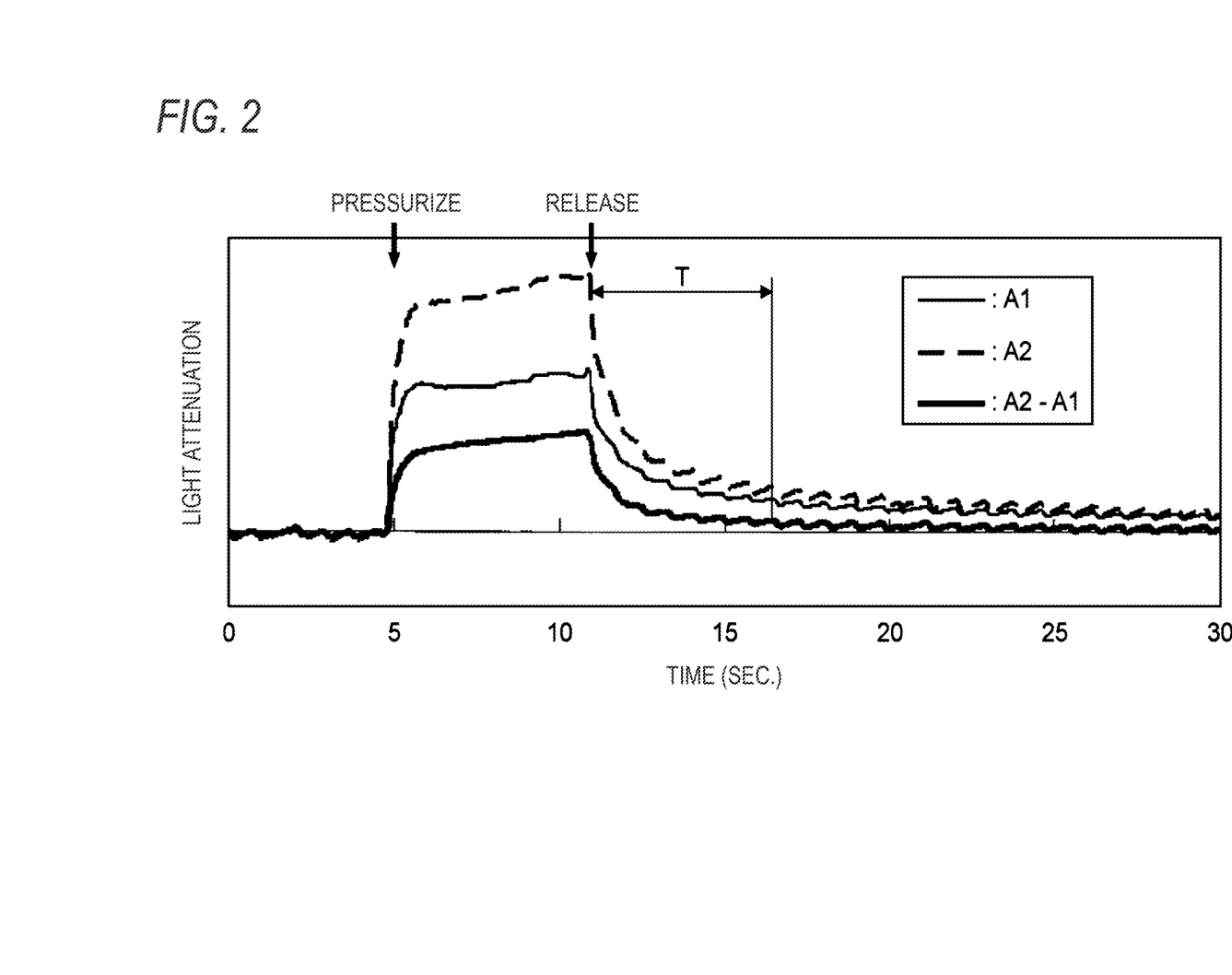
FIG. 2 is a view illustrating an example of a process which is performed by a second calculating section of the biological signal measuring system.

FIG. 2 shows a graph showing temporal changes of the light attenuation A1, the light attenuation A2, and the blood-derived light attenuation Ab (=A2−A1) in the case where the finger 30 is pressed through the probe 20.

It is seen that, even when the pressurization is released, the values of the light attenuations A1, A2 do not return to the levels which are attained before the start of the pressurization, and the deformation of the non-blood tissue exerts influence. It is also seen that, after the release of the pressurization, the difference (A2−A1) of the light attenuations, i.e., the blood-derived light attenuation Ab converges to the level which is attained before the start of the pressurization. Namely, the influence caused by the deformation of the non-blood tissue can be eliminated by a simple calculation process in which the difference of the light attenuations that are obtained by irradiating the living tissue with light beams of different wavelengths is calculated.

The third calculating section 43 is configured so as to identify the blood fill time for filling the living tissue based on the temporal change of the blood-derived light attenuation Ab (=A2−A1) which is acquired by the second calculating section 42, and which is associated with pressurization of the finger 30. Specifically, an adequate threshold is set at which it can be determined that the blood-derived light attenuation Ab approaches to some extent the level that is attained before the start of the pressurization. Then, the time period (T in FIG. 2) elapsing from the timing when the pressurization is released, until the blood-derived light attenuation Ab reaches the threshold is identified as the blood fill time. Therefore, the blood fill time can be correctly identified without being affected by the deformation of the non-blood tissue which is caused by a difference in the degree of pressurization.

The displaying section 14 which is an example of the outputting section is a related-art display device that is disposed on the outer surface of the measuring apparatus 10. The displaying section 14 is communicably connected to the controlling section 12. The controlling section 12 supplies a signal S3 indicative of the blood fill time T determined by the third calculating section 43, to the displaying section 14. The displaying section 14 displays the blood fill time T in an adequate manner corresponding to the signal S3.

When performing a simple work of attaching the existing probe 20 which is to be used in pulse oximetry, to the finger 30 of the subject, and pressing the finger 30 through the probe 20, therefore, a medical person can recognize the blood fill time T which is correctly determined, on the displaying section 14. Namely, the blood fill time T can be identified rapidly and correctly without requiring preparation of a special probe and performing a special work.

The foregoing description of the embodiment has been made in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

The light receiver 22 is not always required to be placed at a position where the light beams which have been passed through the finger 30 can be received. Alternatively, a configuration may be employed where the light receiver is placed at a position where light beams which have been reflected from the finger 30 are received, and the light attenuations are acquired based on the reflection intensities of light beams of different wavelengths.

Figure 3A:
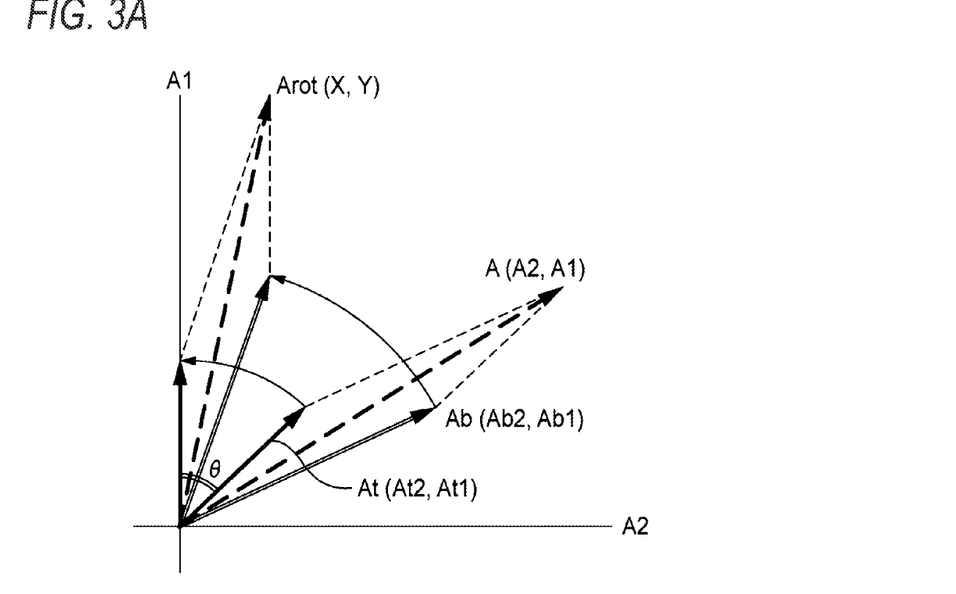
FIGS. 3A and 3B are views illustrating another example of the process which is performed by the second calculating section.
Figure 3B:
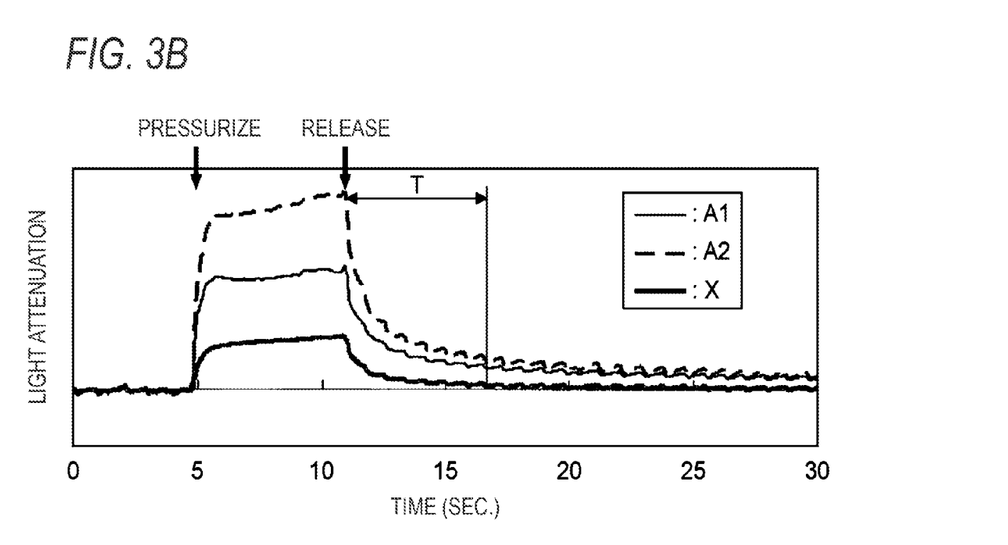

The process in which the second calculating section 42 acquires the blood-derived light attenuation is not always required to be performed based on the difference of the light attenuation A1 and the light attenuation A2. FIGS. 3A and 3B are views illustrating another example of the process which is performed by the second calculating section 42, and in which the rotation matrix is used.

In FIG. 3A, the Y-axis indicates the light attenuation A1 of the first light beam, the X-axis indicates the light attenuation A2 of the second light beam, and the light attenuation A at a certain time is expressed by a vector having components (A2, A1). The vector A is given in the form of a resultant vector of a vector having components (Ab2, Ab1) and indicating the blood-derived light attenuation Ab, and a vector having components (At2, At1) and indicating the light attenuation At derived from the non-blood tissue.

When the vector A is rotated by θ in a coordinate space, a vector Arot is obtained. It is seen that the component derived from the non-blood tissue is eliminated from the X-axis component of the vector Arot, and the vector Arot consists of only the blood-derived component. This operation is expressed by the following expression:

$$Arot^T = KA^T \qquad (6).$$

In the above expression, K and A are expressed by the following matrixes, respectively.

$$K = \begin{pmatrix} \cos\theta & -\sin\theta \\ \sin\theta & \cos\theta \end{pmatrix} \qquad (7)$$

$$A = (A2 \quad A1)$$

The light attenuation At derived from the non-blood tissue does not depend on the wavelength. In FIG. 3A, therefore, At1=At2. Consequently, $\theta = (\pi/2) = -\tan^{-1}(At1/At2)$ is attained.

FIG. 3B shows the temporal change of the value of the X-coordinate of the thus obtained vector Arot together with the temporal changes of the light attenuations A1, A2. It is seen that, even when the pressurization is released, the values of the light attenuations A1, A2 do not return to the levels which are attained before the start of the pressurization, and the light attenuations are affected by deformation of the non-blood tissue. By contrast, it is seen that, after the release of the pressurization, the value of the X-coordinate of Arot, i.e., the blood-derived light attenuation Ab converges to the level which is attained before the start of the pressurization. Namely, the influence caused by deformation of the non-blood tissue can be eliminated by applying a simple rotation calculation to a matrix acquired from the values of light attenuations which are obtained by irradiating the living tissue with light beams of different wavelengths.

In this case, the third calculating section 43 is configured so as to identify the blood fill time for filling the living tissue, based on the temporal change of the blood-derived light attenuation Ab (=X) which is acquired by the second calculating section 42, and which is associated with pressurization of the finger 30. Specifically, an adequate threshold is set at which it can be determined that the blood-derived light attenuation Ab approaches to some extent the level that is attained before the start of the pressurization. Then, the time period (T in FIG. 3B) elapsing from the timing when the pressurization is released, until the blood-derived light attenuation Ab reaches the threshold is identified as the blood fill time. Therefore, the blood fill time can be correctly identified without being affected by the deformation of the non-blood tissue which is caused by a difference in the degree of pressurization.

The third calculating section 43 is not always required to directly identify the blood fill time T from the blood-derived light attenuation Ab which is acquired by the second calculating section 42. As indicated by the broken lines in FIG. 1, for example, the controlling section 12 may include a fourth calculating section 44. The fourth calculating section 44 is configured so as to, as shown in FIGS. 4A and 4B, acquire the differential value Ad of the blood-derived light attenuation Ab which is acquired by the second calculating section 42.

Figure 4A:
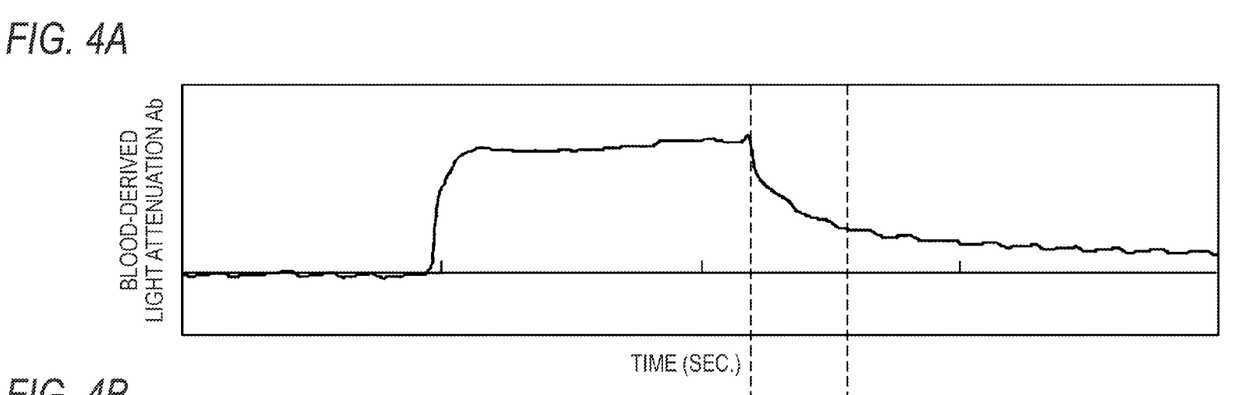
FIGS. 4A and 4B are views illustrating an example of a process which is performed by a fourth calculating section of the biological signal measuring system.
Figure 4B:
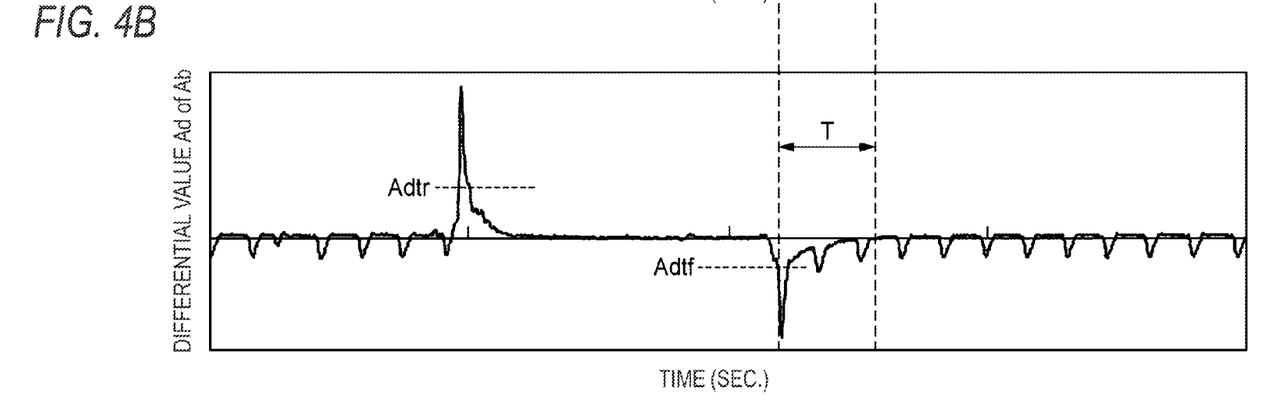

FIG. 4A shows the temporal change of the blood-derived light attenuation Ab which is acquired by the second calculating section 42, and FIG. 4B shows the temporal change of the differential value Ad which is acquired by the fourth calculating section 44. When the light attenuation Ab is rapidly raised because of pressurization of the living tissue, the differential value Ad is largely changed. When blood is evacuated from the place to which pressurization is applied, the light attenuation Ab has a substantially constant value in the vicinity of the maximum value, and therefore the differential value Ad drifts around zero. When the pressurization is then released, the light attenuation Ab is rapidly lowered in accordance with the flow-in of blood, and therefore the differential value Ad is largely changed. In accordance with that the living tissue is filled with blood, the light attenuation Ab converges to a constant value, and also the differential value Ad converges to zero.

In this case, the third calculating section 43 is configured so as to identify the blood fill time T based on the temporal change of the differential value Ad which is acquired by the fourth calculating section 44. Specifically, the time period which elapses after the timing when the differential value Ad reaches a predetermined threshold Adtf in accordance with the release of the pressurization, until the differential value returns to zero is set as the blood fill time T. In place of zero, a threshold according to this value may be set, and the blood fill time T may be identified based on the timing when the differential value reaches this threshold.

Namely, the blood fill time T is identified while attention is focused only on a change in light attenuation after the release of the pressurization. According to the configuration, even under a situation where the reference value of the light attenuation before pressurization is changed as in the example shown in FIG. 6B, the blood fill time T can be correctly identified without being affected by the change.

The fourth calculating section 44 is not limited to have the configuration where the differential value of the blood-derived light attenuation Ab is obtained. For example, the section may have a configuration where the section acquires a signal in which components of frequencies that are lower than a predetermined frequency are removed from a signal indicative of the blood-derived light attenuation Ab that is acquired by the second calculating section 42. Also according to the configuration, effects similar to those described above are attained.

Figure 5:
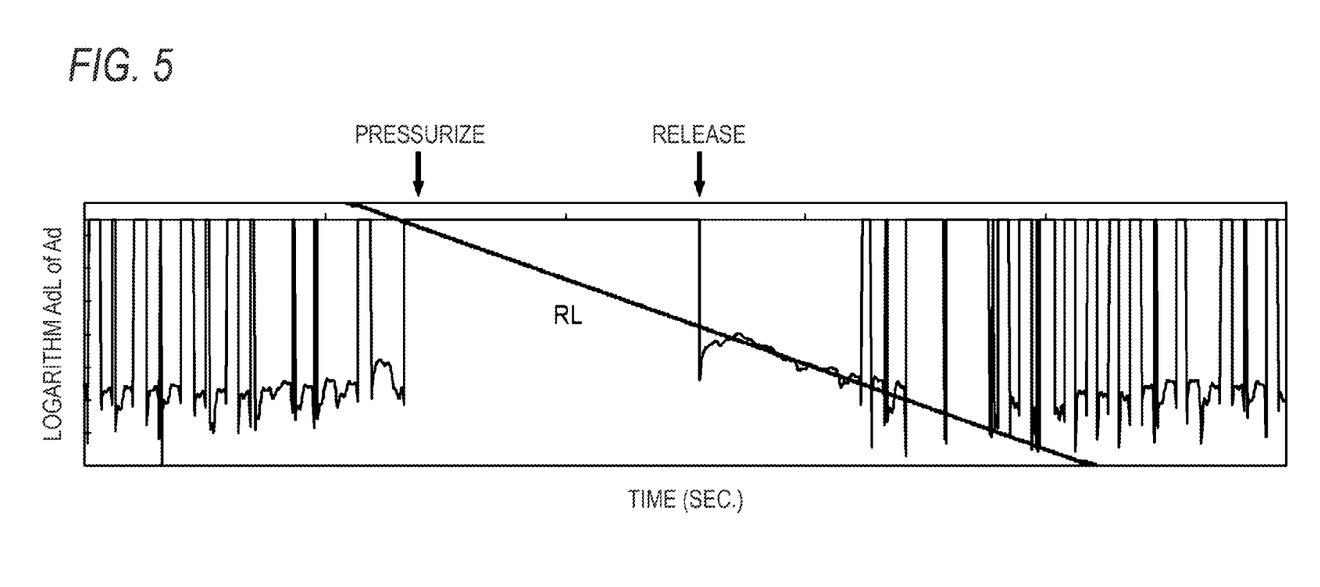
FIG. 5 is a view illustrating an example of a process which is performed by a fifth calculating section of the biological signal measuring system.

The controlling section 12 may further include a fifth calculating section 45. The fifth calculating section 45 is configured so as to obtain the logarithm of the value of the signal acquired by the fourth calculating section 44. FIG. 5 shows the temporal change of the value AdL which is the natural logarithm of the differential value Ad shown in FIG. 4B.

In this case, the third calculating section 43 obtains the regression line L by calculation, from the temporal change of the logarithm AdL after the release of the pressurization, and identifies the reciprocal of the gradient of the regression line, i.e., the time constant, as the blood fill time T.

As shown in FIG. 4B, it is seen that, after the release of the pressurization, the differential value Ad has tendency to converge as a whole to a constant value, but is periodically changed up and down. This is caused by the influence of the pulse. When the fifth calculating section 45 performs a calculation to further acquire the logarithm AdL and obtain the regression line as described above, it is possible to conduct an exponential approximation in which the influence of noises due to the pulse is reduced. Therefore, the blood fill time T can be identified more correctly.

A configuration may be employed where the process of identifying the blood fill time T in the third calculating section 43 is performed when the instruction receiving section 11 receives instructions for starting measurement. Another configuration may be employed where the process is automatically started when the amount of the change of the blood-derived light attenuation Ab acquired by the second calculating section 42 exceeds a predetermined value. The determination on whether the amount of the change of the blood-derived light attenuation Ab exceeds the predetermined value or not may be conducted based on the fact that the light attenuation Ab acquired by the second calculating section 42 exceeds a predetermined threshold, or the fact that the differential value Ad acquired by the fourth calculating section exceeds the predetermined threshold Adtr shown in FIG. 4B.

Usually, such a large change is not produced in the light attenuation Ab as far as usual measurement by pulse oximetry is performed. When a large change occurs in the light attenuation Ab, therefore, it is possible to determine that the possibility that the living tissue is pressed in order to identify the blood fill time is high. In a configuration where the blood fill time is automatically identified based on the determination, the burden on the operator can be further reduced.

As an effect of the presently disclosed subject matter, the unnecessity of preparation of a special probe in the case where the blood fill time T is to be identified has been described. This is not intended to inhibit the use of additional equipment. A configuration may be employed where, as indicated by the broken lines in FIG. 1, a cuff 50 which covers the probe 20 is attached to the finger 30 of the subject, and the controlling section 12 further includes a cuff pressure controlling section 46 which controls the air pressure inside the cuff 50.

The cuff pressure controlling section 46 first pressurizes the interior of the cuff 50 so that the finger 30 of the subject can be pressed at a predetermined pressure through the probe 20. After elapse of a predetermined time period, the interior of the cuff 50 is depressurized. According to the configuration, the pressurization can be always performed under constant conditions irrespective of the operator or the repeat number. Therefore, the blood fill time T can be identified more correctly.

The identified blood fill time T is not always required to be displayed on the displaying section 14 in the form of numerals. In addition to or in place of this, a color or symbol indicative of the blood fill time T may be displayed on the displaying section 14, or a sound indicative of the blood fill time T may be output.

The functions of the first to fifth calculating sections 41 to 45, and cuff pressure controlling section 46 which are described above can be realized by the operation of hardware such as circuit devices, that of software such as programs stored in the computer-readable recording medium or the controlling section 12 which is an example of the computer, or a combination of these operations.

According to an aspect of the presently disclosed subject matter, by performing only a simple calculation process, the blood fill time can be correctly identified while eliminating the influence of the deformation of the non-blood tissue which is caused by a difference in the degree of pressurization. In order to obtain an output of the blood fill time, the operator is requested only to perform a substantial work of attaching an existing probe for pulse oximetry or the like to living tissue of the subject, and pressurizing the living tissue. Namely, the blood fill time can be identified rapidly and correctly without requiring preparation of a special probe and performing a special work.

According to an aspect of the presently disclosed subject matter, the fourth calculating section which is configured to acquire a signal in which a component of a frequency that is lower than a predetermined frequency is removed from a signal indicative of the blood-derived light attenuation may be provided, and the blood fill time may be identified based on a temporal change of the signal which is acquired by the fourth calculating section after the pressurization of the living tissue is released. Thus, the blood fill time is identified while attention is focused only on a change in light attenuation after release of pressurization. Even under a situation where the reference value of the light attenuation before pressurization is changed, therefore, the blood fill time can be correctly identified without being affected by the change.

According to an aspect of the presently disclosed subject matter, the fifth calculating section which is configured to acquire a logarithm of a value of the signal acquired by the fourth calculating section may be provided, and the blood fill time may be identified based on a gradient of a regression line which is obtained from a temporal change of the logarithm after the pressurization of the living tissue is released. Thus, noises which are superimposed on the signal acquired by the fourth calculating section, and which are caused by the pulse or the like can be eliminated, and the blood fill time can be identified more correctly.

According to an aspect of the presently disclosed subject matter, when an amount of the change of the blood-derived light attenuation is larger than a predetermined value, a measurement of the blood fill time may be automatically started. In the case where a large change is made in the blood-derived light attenuation, it is possible to determine that the probability that the living tissue is pressed in order to determine the blood fill time is high. When identification of the blood fill time is automatically performed based on the determination, the burden on the operator can be further reduced.

According to an aspect of the presently disclosed subject matter, the cuff which is adapted to be attached to the subject in a manner that the cuff can pressurize the living tissue and the cuff pressure controlling section which is configured to control an air pressure inside the cuff may be provided. In this case, the pressurization can be always performed under constant conditions irrespective of the operator or the repeat number. Therefore, the blood fill time can be identified more correctly.

What is claimed is:

1. A biological signal measuring system comprising:
   a light emitter which is configured to emit a first light beam having a first wavelength, and a second light beam having a second wavelength;
   a light receiver which is configured to output first and second signals respectively in accordance with received light intensities of the first and second light beams that have been passed through or reflected from a living tissue of a subject;
   a first calculating section which is configured to acquire a light attenuation of the first light beam based on the first signal, and a light attenuation of the second light beam based on the second signal;
   a second calculating section which is configured to acquire a blood-derived light attenuation based on the light attenuation of the first light beam, and the light attenuation of the second light beam;
   a third calculating section which is configured to identify a blood fill time for filling the living tissue, based on a temporal change of the blood-derived light attenuation associated with pressurization of the living tissue; and an outputting section which is configured to output the identified blood fill time, wherein the blood fill time is defined as a time period elapsing from a release of pressurization of the living tissue until the blood-derived light attenuation reaches a predetermined threshold.

2. The biological signal measuring system according to claim 1, wherein the second calculating section acquires the blood-derived light attenuation based on a difference of the light attenuation of the first light beam and the light attenuation of the second light beam.

3. The biological signal measuring system according to claim 1, wherein the second calculating section applies a rotation matrix to the light attenuation of the first light beam and the light attenuation of the second light beam, thereby acquiring the blood-derived light attenuation.

4. The biological signal measuring system according to claim 1, further comprising a fourth calculating section which is configured to acquire a signal in which a component of a frequency that is lower than a predetermined frequency is removed from a signal indicative of the blood-derived light attenuation, wherein the third calculating section identifies the blood fill time based on a temporal change of the signal which is acquired by the fourth calculating section after the pressurization of the living tissue is released.

5. The biological signal measuring system according to claim 4, further comprising a fifth calculating section which is configured to acquire a logarithm of a value of the signal acquired by the fourth calculating section, wherein the third calculating section identifies the blood fill time based on a gradient of a regression line which is obtained from a temporal change of the logarithm after the pressurization of the living tissue is released.

6. The biological signal measuring system according to claim 1, wherein when an amount of the change of the blood-derived light attenuation is larger than a predetermined value, a measurement of the blood fill time by the third calculating section is automatically started.

7. The biological signal measuring system according to claim 1, further comprising:

a cuff which is adapted to be attached to the subject in a manner that the cuff can pressurize the living tissue; and a cuff pressure controlling section which is configured to control an air pressure inside the cuff.

8. A method of controlling the biological signal measuring system of claim 1 comprising:

acquiring the light attenuation of the first light beam based on the first signal, and the light attenuation of the second light beam based on the second signal;

acquiring the blood-derived light attenuation based on the light attenuation of the first light beam, and the light attenuation of the second light beam;

identifying the blood fill time for filling the living tissue, based on a temporal change of the blood-derived light attenuation associated with pressurization of the living tissue; and outputting the identified blood fill time.

9. A non-transitory computer-readable medium storing a program that, when executed, causes a computer to perform the method according to claim 8.

* * * * *

UNITED STATES PATENT AND TRADEMARK OFFICE
CERTIFICATE OF CORRECTION

PATENT NO. : 9,521,969 B2
APPLICATION NO. : 14/161566
DATED : December 20, 2016
INVENTOR(S) : Hirabara et al.

It is certified that error appears in the above-identified patent and that said Letters Patent is hereby corrected as shown below:

In the Specification

Column 5, Line 41: replace "$(cm^{-1})$" with --(cm)--.

Signed and Sealed this
Fourteenth Day of March, 2017

Michelle K. Lee
*Director of the United States Patent and Trademark Office*